United States Patent [19]

Williams

[11] 4,362,241
[45] Dec. 7, 1982

[54] APPARATUS FOR COLD DISINFECTION OF DENTAL AND MEDICAL INSTRUMENTS

[76] Inventor: Robert M. Williams, 705 Kenyon St., NW., Washington, D.C. 20010

[21] Appl. No.: 175,633

[22] Filed: Aug. 6, 1980

[51] Int. Cl.³ .............. B65D 81/32; B65D 30/22; A61L2/00; B65D 81/24
[52] U.S. Cl. .................. 206/210; 206/219; 206/524.3; 422/300
[58] Field of Search .............. 206/207, 206/208, 210, 205, 209.1, 525, 213.1, 524.3, 219; 422/300

[56] References Cited

U.S. PATENT DOCUMENTS

| | | | |
|---|---|---|---|
| 1,196,571 | 8/1916 | Martocci-Pisculli | 422/300 |
| 1,342,968 | 6/1920 | Moolten . | |
| 1,539,253 | 6/1923 | Fuller . | |
| 1,742,061 | 4/1923 | Curry . | |
| 1,904,609 | 4/1933 | Breadon | 206/209.1 |
| 2,041,077 | 5/1936 | Lininger . | |
| 2,073,137 | 3/1937 | Bimrose . | |
| 2,340,206 | 1/1944 | Richards | 422/300 |
| 3,342,544 | 9/1967 | Curiel | 422/300 |
| 3,367,785 | 2/1968 | Finucane et al. | 206/525 |
| 3,939,971 | 2/1976 | Tulis | 206/205 |
| 4,021,197 | 5/1977 | Brooks | 206/207 |
| 4,211,323 | 7/1980 | Olsen | 206/210 |
| 4,209,013 | 6/1980 | Alexander | 128/213A |

FOREIGN PATENT DOCUMENTS 2060399 5/1981 United Kingdom.

*Primary Examiner*—William T. Dixson, Jr.
*Attorney, Agent, or Firm*—Beveridge, DeGrandi & Kline

[57] ABSTRACT

Apparatus for the cold disinfection of dental and medical instruments includes an envelope of water impervious material and a cold disinfection solution. The envelope may be deformable with a gauze liner bonded within it, and with the solution, or its components, in crushable capsules. In alternate embodiments, the envelope may have a gauze liner bonded to it and saturated with the solution, and the envelope sealed, or the envelope may contain the solution or its components in one or more capsules and with no gauze liner. A further embodiment provides a support for an instrument encased in a gauze sleeve and a reservoir having valved discharge nozzles directed towards the gauze-encased instrument.

10 Claims, 7 Drawing Figures

APPARATUS FOR COLD DISINFECTION OF DENTAL AND MEDICAL INSTRUMENTS

BACKGROUND OF THE INVENTION

The present invention relates to apparatus for disinfecting medical and dental instruments utilizing a cold disinfection solution.

It is well recognized in the medical and dental fields that diseases are communicated to patients, and between patients, by various harmful organisms, such as spores, viruses, bacteria and fungus, as well as other pathogenic microorganisms. The destruction of these pathogenic microorganisms has been by such means as dry heat and steam, and in more recent times there have been developed various chemicals for the disinfection and sterilization of instruments.

A recent advance in the disinfection of instruments by chemical action has been the acceptance of aqueous solutions of glutaraldehyde, which is sold under such trade names as "Sporicidin" and "Cidex 7". This cold disinfection solution is sold with a buffer, which is required to be mixed with it in order to activate the solution. The activated solution is poured into a tray, and the instruments are immersed in the solution for a period of from almost seven to ten hours, for sterilization, and ten minutes for disinfection. The preparation of the solution and the immersion of instruments in trays is time consuming, and is not acceptable in cases where instruments have moving parts, bearing, and the like, which might be harmed by immersion, and the entry of the solution into the interior of the instrument. Further, in this procedure, the instruments must be disassembled, and then reassembled after disinfection. These steps add to the costs.

The problem existing in dentistry of carrying infection from one patient to another by the hand pieces or dental tools, such as drills, is recognized, and there have been proposals to provide discardable shields or protectors on such hand pieces. Examples of such proposals are: U.S. Pat. Nos. Moolten 1,342,968, Fuller 1,539,253, Curry 1,742,061, Lininger 2,041,077 Bimrose 2,073,137. These disclosures provides for the covering or isolation of an infected hand piece, rather than the disinfection and sterilization of it.

SUMMARY OF THE INVENTION

The present invention provides for the contacting of the exterior of medical and dental instruments with cold disinfection solution, on an individual basis. In a preferred embodiment, an envelope is provided of liquid-impervious material, having a generally elongate shape, and divided transversely into a pair of chambers. One chamber has an entry thereinto from an end of the envelope, and in this chamber there is a liner of liquid absorbent material, which is bonded to the interior of the envelope, and in the second chamber there are crushable capsules containing the cold sterilization solution, and its buffer or activater, where required. Communication is provided so that liquid may flow from the one chamber into the chamber with the liner. The envelope is of a readily deformable material, such as a thin plastic sheet material, whereby before or after permeation of the liner with the cold disinfection solution, an instrument may be inserted through the entry into the envelope, and the envelope deformed or crushed so as to conform to the exterior of the instrument, whatever its shape, thereby bringing the solution into direct contact with the entire outer surface of the instrument which in use would contact the patient. In a first alternate embodiment, the envelope has a single compartment, in which is the liquid absorbent liner, saturated with the cold disinfection solution; the entry into the envelope is provided by a releasable seal. In a further embodiment, the envelope is provided with two chambers, one chamber containing the capsules for the cold disinfection solution and the other chamber having an entry thereinto which is sealable, but having no liquid absorbent liner in it, such embodiment being usable where the instrument has no entry into the interior of it, such as where the instrument is a thermometer. Yet another embodiment provides a support for a reservoir, the reservoir having an opening through which an instrument, such as a dental hand piece, may be placed, resting against a side of the opening of the reservoir and being encased in an absorbent sleeve, such as a gauze sock which engages the entire outer surface of the instrument. The reservoir contains valved nozzles directed towards the instrument when it is in position within the opening of the reservoir.

DESCRIPTION OF THE PREFERRED EMBODIMENTS

Figure 1:
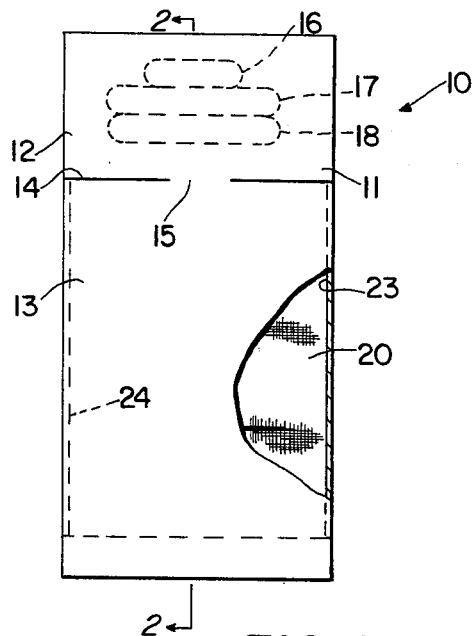
FIG. 1 is an elevational view of an envelope and related components in accordance with the present invention.

Referring now to the drawings, wherein like or corresponding reference numerals are used to designate like or corresponding parts throughout the several views, there is shown in FIG. 1 a device 10 which includes an envelope 11. Envelope 11 is of a liquid impervious, flaccid material, and thereby prevents the escape of liquid from it, and is deformable or crushable about an instrument or object which is placed within it, so as to conform substantially to the exterior shape of such object. A suitable material for the envelope 11 is polyethylene, which is heat sealable. The envelope 11 is divided into a first chamber 12, and a second chamber 13. The division of the envelope is by a heat seal 14 which extends partially across the width of the envelope 11, there being a gap 15 in the portions of heat seal 14 so as to provide communication between the chambers 12 and 13.

In the first chamber 12, there may be seen three crushable capsules 16, 17, and 18, these containing an aqueous solution of glutaraldehyde and a buffer (activater) for it, these materials being provided in appropriate quantity relationships within the noted crushable capsules. Within the second chamber 13 is a liner 20 which is liquid absorbent, preferably of gauze material, the liner 20 being bonded to the envelope 11.

Figure 2:
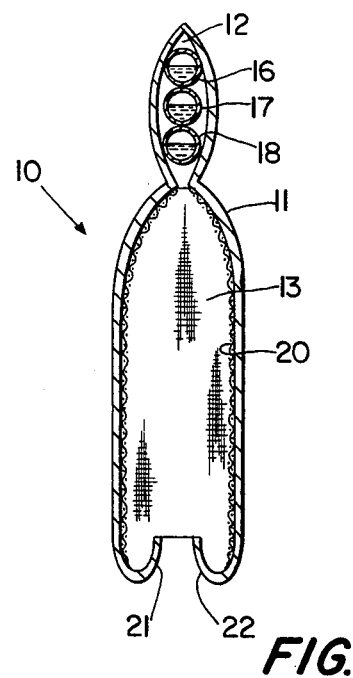
FIG. 2 is a cross-sectional view taken on the line 2—2 of FIG. 1.

Referring now to FIG. 2, there may be seen the envelope 11 with the first chamber 12 and the capsules 16, 17, and 18, and the second chamber 13, with the liner 20 therein. The envelope 11 at its lower end, as shown in FIG. 2, has an entry defined by inwardly turned edges 21 and 22, which provide inwardly turned cuffs which captures between each cuff and the major wall portion of the envelope 11 forming the second chamber 13 the bottom end or edge of the liner 20. The inwardly turned edges or cuffs 21 and 22 may be heat sealed, thereby bonding the lower edge of the liner 20 between them. Because of the self-adherent nature of the material of which the envelope 11 is made, after manufacture, and in preparation for shipment, the cuffs 21 and 22 may be pressed against each other, so as to seal the interior of the envelope 11 against the entry of undesired materials. FIG. 2 show the edges or cuffs 21 and 22 spaced apart, which is the position that they will take in preparation for receiving an instrument for disinfection.

The liner 20 is made up, as shown in FIG. 2, of a pair of walls, each adjacent a wall of the portions of envelope 11 forming the second chamber 13. The upper portions of the walls of the liner 20 may be joined or integral, or may be separate, when initially made, and these walls may be joined or not at the lateral edges thereof shown in FIG. 1. Preferably, the liner 20 is bonded not only along the heat seal 14, but along the lateral edges 23 and 24 of the envelope 11. The lower ends of the walls of the liner 20 provide an entry into the chamber 13, which is in registry with the entry provided by the inwardly turned edges or cuffs 21 and 22.

Figure 3:
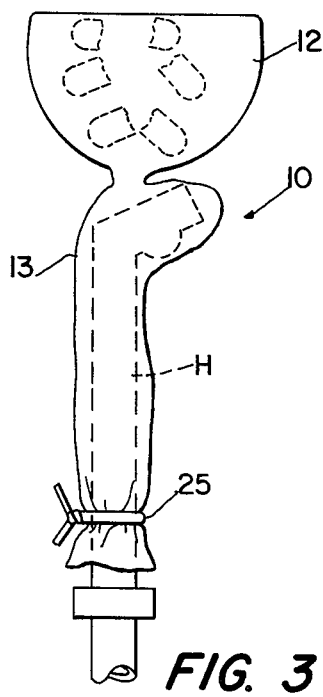
FIG. 3 is a view showing the envelope of FIGS. 1 and 2 in use on a dental hand piece.

Referring now to FIG. 3, there is shown the device 10 in use and in position on a dental instrument, specifically a dental handpiece H. The entry provided by the cuffs 21 and 22 and the lower portions of the liner 20 will have been opened, and the device 10 moved downwardly over the dental hand piece H. The readily manually crushable capsules 16, 17 and 18 will then have been crushed, the fragments being indicated by the dashed lines in the first chamber 12 in FIG. 3. The crushing of the capsules 16, 17 and 18 has released the cold disinfection solution and its buffer or activater, and the activated solution will have passed from the chamber 12 into the chamber 13, and permeated the liner 20. The device 10 will then have been sealed and secured to the hand piece H by a tie device 25. Then the device 10 will have been deformed or crushed so as to substantially conform to and engage the entire outer surface of the hand piece H. In this way, the cold disinfection solution is and will remain in contact with substantially the entire outer surface of the hand piece H for the requisite time for this disinfection, and for sterilization, where desired.

It will be understood that there has been shown specifically a dental hand piece H, which is illustrative of an instrument which is desirably disinfected and sterilized, but is not amenable to immersion. Other dental or medical instruments may be utilized with the herein disclosed devices, as will be readily understood.

Whatever the instrument, and its exterior shape, due to the bonding or adhering of the liner 20 to the envelope 11 in the manner hereinabove disclosed, the entry of the instrument into the second chamber 13 will not dislodge the liner, and neither will the withdrawal of the instrument from the device 10 dislodge the liner.

Figure 4:
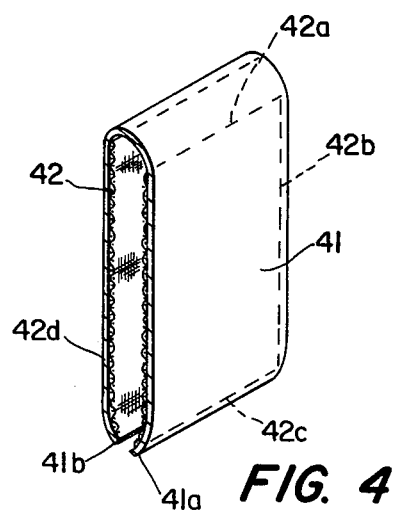
FIG. 4 is a perspective view, partly in cross-section, of a further embodiment of the present invention.

In FIG. 4 there is shown an alternate embodiment, the device 40 shown therein comprising an envelope 41 defining but a single chamber, and having therein a gauze liner 42 which is bonded to the envelope 41 along an upper line 42a, a lateral edge 42b and an edge opposite to the edge 42b, which is not shown in FIG. 4. There is also a bonding of the liner 42 along a pair of lower lines 42c and 42d which extend generally parallel to the lower edges 41a and 41b at the lower end of the envelope 41. The lower portions of the two walls of the liner 42 and the lower portions of the walls forming the envelope 41 provide, in registry, an entry into the device 40. The lower edge of the liner 42 does not extend downwardly beyond the lines 42c and 42d, and therefore below these edges there is provided on the envelope 41 a sealing zone at the entry, which may be provided by the material of which envelope 41 is made, or by some additional material applied to the inner lips of the lower portions of the walls of the envelope 41, such material being a releasable sealant, and providing for hermetic sealing of the interior of the envelope 41. In this embodiment, the cold disinfectant solution has been provided within the device 40, so as to permeate the liner 42, after which the device 40 is sealed.

In use, the device 40, sealed as indicated and with the absorbent liner 42 permeated with the noted cold disinfection solution, is opened at the seal, so as to provide an entry, and then objects to be disinfected are inserted within the device 40 or the device 40 is placed over such an object, and is then deformed, as necessary, so that the entire outer surface of the object is engaged by the permeated or saturated liner 42.

Figure 5:
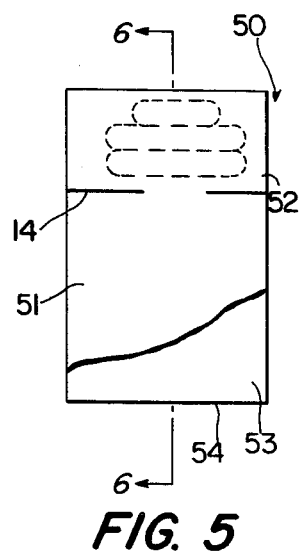
FIG. 5 is an elevational view of an embodiment similar to FIG. 1.
Figure 6:
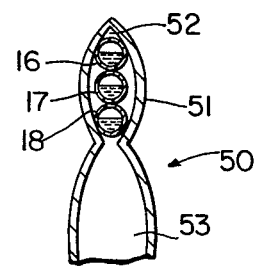
FIG. 6 is a cross-sectional view taken on the line 6—6 of FIG. 5.

In FIG. 5, there is shown a device 50 in accordance with the present invention and comprising an envelope 51 of the same material as the envelope 11, being divided into an upper chamber 52 and a lower chamber 53 by a heat seal 14 extending partially across the envelope. Within the first chamber 52 are capsules 16, 17 and 18 which contain the same materials, and have the same attributes as the capsules 16, 17 and 18 of the embodiment shown in FIGS. 1-3. In the embodiments of FIGS. 5 and 6, the second chamber 53 is not provided with a liner, but at its lower end has a seal zone indicated generally by the reference numeral 54, provided at the lower ends of the walls forming the second chamber 53, and being positioned so as to seal the entry into the second chamber 53.

In use, an instrument or other object is inserted into the chamber 53, and utilizing the sealing zones 54 and the adhesive qualities thereof, sealing is effected about the instrument or object, or sealing is effected between the two zones 54 if the instrument is of such size as to be completely housed or contained within the chamber 53. Such an instrument may be, for example, a thermometer, or some other instrument which would not be harmed by immersion. Thereafter, the crushable capsules are broken, and the cold disinfection solution is activated and caused to flow into the chamber 53 where it contacts and disinfects the object, or sterilizes the object, if contact is of sufficient length of time.

Figure 7:
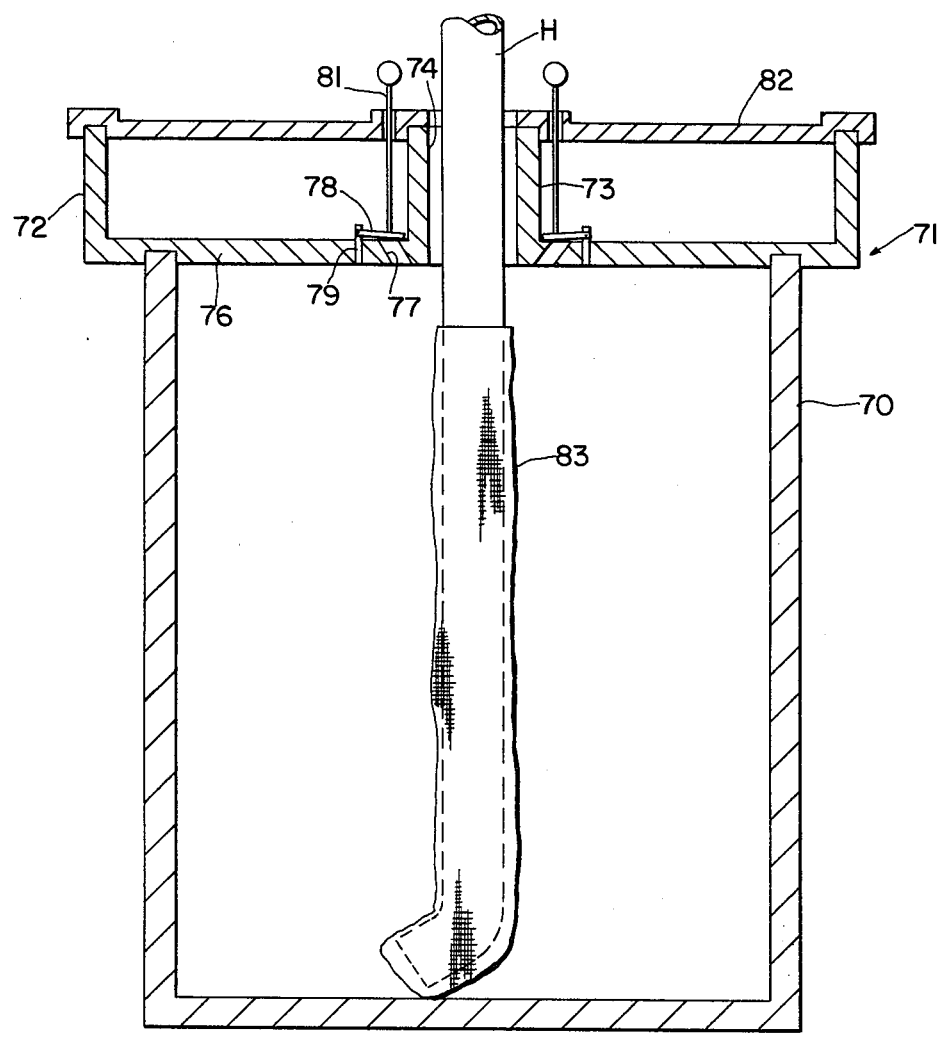
FIG. 7 is a transverse cross-sectional view of another embodiment of the present invention, with an instrument in place.

Referring now to FIG. 7, there is shown an alternate embodiment of the present invention. A support 70, preferably in the form of a container, is provided, and has a reservoir 71 at its upper end and positioned on it. The reservoir 71 includes an outer wall 72 and an inner wall 73 concentric with it. Thus there is provided a central opening 74 which is of a size to receive an instrument, such as a dental hand piece H. The reservoir 71 includes a bottom wall 76, in which there are openings 77 which provide nozzles which are inwardly directed, and which surround the opening 74. Suitable valves and valve controls are provided for the openings 77, there being shown a resilient flap valve 78 suitably secured at one end by a rivet 79 to the bottom wall 76. A handle 81 extends upwardly from the resilient flap valve 78, so that when it is lifted upwardly, it will permit flow of liquid from the reservoir 71 outwardly through the openings, and being directed in a generally conical fashion. The reservoir 71 includes an appropriate cover 82.

In use, a sock or sleeve of liquid absorbent material, such as the gauze sock 83, is provided on the dental hand piece H. Then the thus encased hand piece H is inserted into the opening 74 in the reservoir 71, resting upon the bottom of the supporting container 70. One or more of the valve handles 81 are then operated, so as to release the cold disinfection solution contained in the reservoir 71 through the opening or openings 77, so as to engage and permeate or saturate the gauze sock 83, thereby causing the cold disinfection solution to be in contact with all portions of the exterior surface of the dental hand piece H.

There have been provided devices for utilization with cold disinfection solution for engaging the entire outer surface of an object to be disinfected or sterilized. Each of the device is readily fabricated, and is inexpensive, providing disinfection and/or sterilization, without immersion where immersion is undesirable.

It will be obvious to those skilled in the art that various changes may be made without departing from the spirit of the invention, and therefore the invention is not limited to what is shown in the drawings and described in the specification but only as indicated in the appended claims.

I claim:

1. A device for disinfecting dental and medical objects, including instruments, comprising,
   an envelope of liquid impervious material, said envelope having an opening which permits the entry of an object into the envelope,
   a liquid absorbent liner located in said envelope, said liner having an opening which permits the entry of an object into the liner within said envelope, said absorbent liner facing inwardly and being exposed to make physical contact with an object placed within said liner,
   said liner being attached to the envelope near the opening of the liner retaining the liner in position relative to the envelope when an object is being inserted into the envelope,
   a cold disinfectant solution located in said envelope for impregnating said absorbent liner,
   said envelope and said liner being of flaccid material permitting their deformation and enabling said liner to conform to the outer surface of an object therewithin,
   said opening of said envelope being sealable to retain the object in the envelope and preventing the loss of said cold disinfectant solution from said envelope and impregnated liner.

2. The device of claim 1 wherein said liner is bonded to said envelope remote from the opening of the envelope.

3. The device of claim 1 wherein said liner is formed of gauze.

4. The device of claim 1 wherein said envelope has a portion turned inwardly into the opening of said liner.

5. The device of claim 1 wherein said envelope has a first chamber and a second chamber, means providing communication between said chambers, and manually crushable capsule means in said first chamber having said cold disinfectant solution therein.

6. The device of claim 5 wherein said envelope is formed of heat sealable plastic material, said envelope having a heat seal extending partially thereacross between said chambers.

7. The device of claim 5 wherein said capsule means comprises plural capsules, and wherein at least one said capsule contains a said solution and at least one said capsule contains a buffer for said solution.

8. The device of claim 5 wherein said envelope and said liner are elongate, said opening of the envelope being at one end of said envelope and opening into said second chamber, said first chamber being at an end of the envelope which is opposite said opening of the envelope.

9. The device of claims 1 or 2 or 3 or 4 or 5 wherein said cold disinfectant solution is an aqueous solution of glutaraldehyde.

10. The device of claim 1 or 2 or 3 or 4 or 5 wherein the envelope includes a self adherent material at the opening thereof which renders the opening sealable.

* * * * *